(12) United States Patent
Eichenlaub et al.

(10) Patent No.: US 12,347,092 B2
(45) Date of Patent: Jul. 1, 2025

(54) DEVICES, SYSTEMS, AND METHODS FOR VIRTUAL BULK DENSITY SENSING

(71) Applicant: FRITO-LAY NORTH AMERICA, INC., Plano, TX (US)

(72) Inventors: Sean Eichenlaub, McKinney, TX (US); Kevin Kaichu Lin, Plano, TX (US)

(73) Assignee: Frito-Lay North America, Inc., Plano, TX (US)

( * ) Notice: Subject to any disclaimer, the term of this patent is extended or adjusted under 35 U.S.C. 154(b) by 453 days.

(21) Appl. No.: 17/840,301

(22) Filed: Jun. 14, 2022

(65) Prior Publication Data

US 2022/0414864 A1 Dec. 29, 2022

Related U.S. Application Data

(60) Provisional application No. 63/215,164, filed on Jun. 25, 2021.

(51) Int. Cl.
*G06T 7/00* (2017.01)
*G01N 33/02* (2006.01)

(52) U.S. Cl.
CPC .......... *G06T 7/0008* (2013.01); *G01N 33/02* (2013.01); *G06T 2207/20081* (2013.01); *G06T 2207/20084* (2013.01); *G06T 2207/30128* (2013.01)

(58) Field of Classification Search
CPC ......... G06T 7/0008; G06T 2207/20081; G06T 2207/20084; G06T 2207/30128; G01N 33/02; A23P 30/20; G05B 13/0265
See application file for complete search history.

(56) References Cited

U.S. PATENT DOCUMENTS

| | | | | |
|---|---|---|---|---|
| 2018/0322436 A1* | 11/2018 | Sotiroudas | ............ | A01M 1/026 |
| 2020/0166909 A1* | 5/2020 | Noone | .................... | G06N 20/00 |
| 2020/0405255 A1* | 12/2020 | Chen | ...................... | A61B 6/461 |
| 2022/0287498 A1* | 9/2022 | Hua | ........................ | G06V 20/68 |
| 2024/0061403 A1* | 2/2024 | Winkler | ........... | G05B 19/41875 |
| 2024/0381881 A1* | 11/2024 | Birkhofer | .............. | A22B 5/007 |

FOREIGN PATENT DOCUMENTS

| | | | | | |
|---|---|---|---|---|---|
| EP | 3671494 A1 | * | 6/2020 | ............ | G06F 30/20 |
| EP | 3939436 | | 1/2022 | | |
| EP | 3939436 A1 | * | 1/2022 | .............. | A23J 3/227 |
| WO | 2020/207293 | | 10/2020 | | |
| WO | 2020/227383 | | 11/2020 | | |

OTHER PUBLICATIONS

International Search Report and Written Opinion issued on Apr. 6, 2023 in PCT/US2022/050669.
International Preliminary Report on Patentability issued on Dec. 26, 2024 in PCT/US2022/050669.

* cited by examiner

*Primary Examiner* — Iriana Cruz
(74) *Attorney, Agent, or Firm* — Barnes & Thornburg LLP; Steven D. Shipe

(57) ABSTRACT

Devices, systems, and methods for real-time food production are disclosed. Extrusion can include including evaluating and controlling one or more production devices to produce desirable food products. Evaluation can be performed by an evaluation system including a convolutional neural network to determine a bulk density value. Control can be performed by a machine learning model on the basis of the bulk density value. Control can include determination of real-time settings for production device parameters.

24 Claims, 10 Drawing Sheets
(1 of 10 Drawing Sheet(s) Filed in Color)

JUMBO PUFFS

SAMPLE SIZE: (SIZE INDIVIDUAL METHODS)

| APPEARANCE | | 0 = GREEN | 1 = GREEN ALERT | 2 = GREEN TAKE ACTION | 3 = RED TAKE ACTION | 4 = RED ABORT | | |
|---|---|---|---|---|---|---|---|---|
| SENSORY APPEARANCE | WITH REFERENCE | | | | | | | |
| | WITHOUT REFERENCE | ☐ SUSTAIN | | ☑ TAKE ACTION | | | | |

| DATE | TIME | SHIFT | LINE |
|---|---|---|---|
| | ONE MOMENT IN | | |

COMMENTS: ROUGH

| | VALUE | GREEN | X | GREEN X | YES/NO | RED TAKE ACTION | X |
|---|---|---|---|---|---|---|---|
| BULK DENSITY (1) | 2 | 2 | | 1-2 | X | N/A | N/A |
| DIAMETER | 18 | 18 | X | 17-18 | N/A | 17,19 | <17, >19 |
| CURL | 27 | 27 | X | 24-29 | N/A | 23,31 | <23, >31 |
| LENGTH | 69 | 69 | X | 66-72 | N/A | 64,74 | <34, >74 |
| SURFACE ATTRITION (2) | 0 | | X | N/A | N/A | >G | N/A |

(1) MEASURE BULK DENSITY FROM SAMPLE COLLECTED BEFORE THE OVEN (COMPOSITE OF ALL EXTRUDERS)
(2) USE JOB 10-100X MORE ALL THE TIME

FIG. 2A

EXTRUDER ADJUSTMENTS

| | BULK DENSITY | DIAMETER | LENGTH | % WATER | CELL SIZE | BLISTER | HARDNESS | ROUGHNESS OF SURFACE | OIL PICKUP |
|---|---|---|---|---|---|---|---|---|---|
| MEAL INCREASE | ↓ | ← | → | ← | ↑ | ← | ← | → | → |
| WATER INCREASE | ↑ | → | ← | → | — | — | ← | → | → |
| SCREW SPEED INCREASE | ↓ | → | → | ← | ↓ | → | → | ← | ← |
| BARREL TEMP | ↓ | ← | ← | ← | ↓ | → | → | ← | — |
| CUTTER SPEED | ↑ | — | → | — | — | — | — | — | — |

FIG. 2C

JUMBO PUFFS

SAMPLE SIZE: (SIZE INDIVIDUAL METHODS)

| APPEARANCE | | 0 = GREEN | 1 = GREEN ALERT | 2 = GREEN TAKE ACTION | 3 = RED TAKE ACTION | 4 = RED ABORT |
|---|---|---|---|---|---|---|
| SENSORY APPEARANCE | WITH REFERENCE | ☐ SUSTAIN | | ☑ TAKE ACTION | | |
| | WITHOUT REFERENCE | | | | | |

| DATE 3-5-19 | TIME 9:00 | SHIFT | LINE |
|---|---|---|---|
| CODE DATE | COMPLETED BY: | | |
| OPERATOR | | | |
| UPC CODE | | | |

COMMENTS: ROUGH

| | VALUE | GREEN | GREEN X | YES/NO | RED TAKE ACTION | X |
|---|---|---|---|---|---|---|
| CODEC BULK DENSITY (1) | 2 | 1-2 | X | N/A | N/A | <1 >2 |
| DIAMETER | 18 | 17-18 | X | N/A | 17,19 | <17 >19 |
| CURL | 27 | 24-29 | X | N/A | 23,31 | <23 >31 |
| LENGTH | 69 | 66-72 | X | N/A | 64,74 | <34 >74 |
| SURFACE ATTRITION (2) | 0 | | X | N/A | >G | N/A |

(1) MEASURE BULK DENSITY FROM SAMPLE COLLECTED BEFORE THE OVEN (COMPOSITE OF ALL EXTRUDERS)
(2) USE JOB 0.1% OF ALL; ONE MOMENT IN TIME

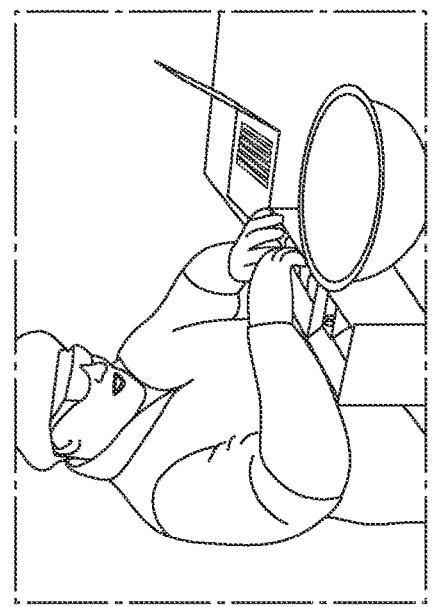

FIG. 3

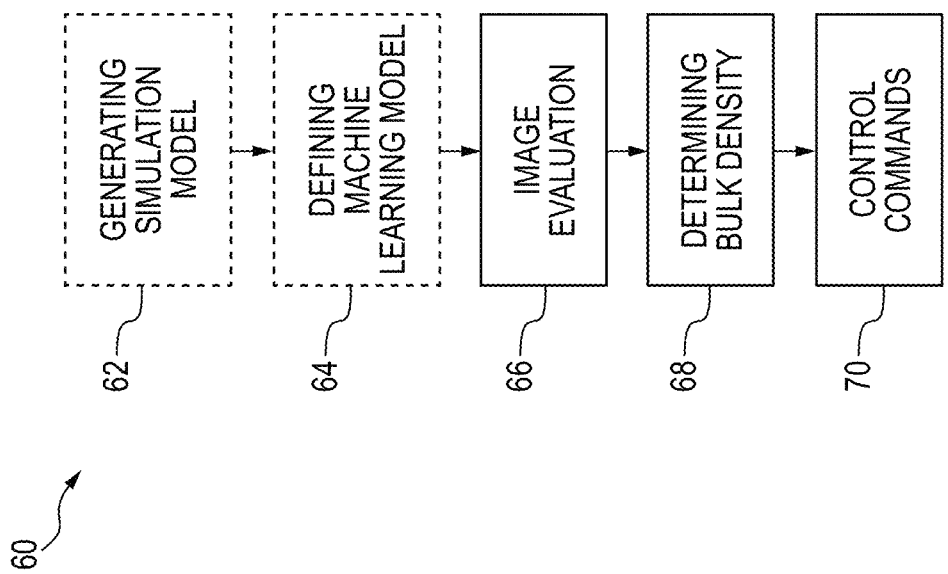

DEVICES, SYSTEMS, AND METHODS FOR VIRTUAL BULK DENSITY SENSING

CROSS-REFERENCE

This Utility Patent Application claims the benefit of priority to Provisional Application No. 63/215,164, filed on Jun. 25, 2021, entitled "DEVICES, SYSTEMS, AND METHODS FOR VIRTUAL BULK DENSITY SENSING," the contents of which is hereby incorporated by reference in its entirety, including but without limitation, those portions related to interfacing.

FIELD

The present disclosure relates to devices, systems, and methods for virtual sensing and more particularly to devices, systems, and methods for virtual sensing for food products.

High volume food production can be challenging to perform while maintaining high quality control. Lag times in product sample testing can be burdensome and/or may fail to provide responsiveness to achieve efficient and/or effective product outcomes. Even traditional automation can face constraints. Improving food production control to consider real-time, or near-real time operations can assist in overcoming such challenges.

SUMMARY

According to an aspect of the present disclosure a system for producing food product may include at least one food product processing device for extruding food material into food products; a bulk density evaluation system for analyzing image information of at least one of food material and food product to determine a bulk density value; and a control system configured to govern operation of the at least one food product processing device based on the determined bulk density value. The control system may include a machine learning model configured to determine, in real-time, at least one control parameter for the at least one food product processing device, based on the determined bulk density value.

In some embodiments, the at least one control parameter is selected from the group comprising meal feed rate, water feed rate, screw speed, barrel temperature, barrel pressure, and cutter speed. The machine learning model may be defined based on a simulation model comprising a physical simulation of food material within the at least one food product processing device. The simulation model may include line data of produced food product.

In some embodiments, the physical simulation of food material may be applied as a reduced order model. The simulation model may include the physical simulation defined by the reduced order model. The machine learning model may include a reinforcement learning model.

In some embodiments, the simulation model may be configured to provide training datasets applied by the machine learning model to generate numerical coefficients for operation of the machine learning model to govern operation of the at least one food product processing device based on the determined bulk density value. The training datasets applied by the machine learning model may be generated in the simulation model. The machine learning model may be formed as a reinforcement model achieving reward reinforcement based on the simulation model to define the reinforcement model.

In some embodiments, reward reinforcement may be determined based on at least one of size, surface attrition, texture, bulk density, and curvature of the food product. Such aspects may be applied in terms of their contribution to, for example as predicted by, sphericity and/or excluded volume. The simulation model may be combined with a mass and energy balance of the at least one food product processing device to provide the training datasets.

In some embodiments, the bulk density evaluation system may include at least one camera for capturing visual images of the food product for analysis. The at least one camera may be arranged to capture visual images of food material within the at least one food product processing device. The at least one camera may be arranged to capture visual images of food product produced from the at least one food product processing device.

In some embodiments, the bulk density evaluation system may include a convolution neural network for analysis of image information. The output of the convolutional neural network may yield determination of at least one of size, surface attrition, texture, bulk density, and curvature of the food product as a numerical output value. The food product produced by the at least one food product processing device may be produced in a prepared form, safe for consumption.

According to another aspect of the present disclosure, a method of operating a system for producing food product including one or more food product processing devices for producing food material as food products may include generating a simulation model based on a physical simulation of food material within the at least one food product extrusion device; defining a machine learning model based on the simulation model for governing control of the at least one food product processing device; evaluating image information of at least one of food material and food product to determine a bulk density value; operating the defined machine learning model to determine, in real-time, desired setting of at least one control parameter for the at least one food product processing device based on the determined bulk density value; and controlling the at least one food product processing device to have the at least one desired control parameter.

In some embodiments, one or more of evaluating image information of at least one of food material and food product, operating the defined machine learning model to determine at least one control parameter in real-time, and controlling the at least one food product processing device to have the at least one desired control parameter may occur recurrently. Generating the simulation model based on a physical simulation of food material may include defining the simulation model from a reduced order model based on the physical simulation of the at least one food product processing device.

In some embodiments, generating the simulation model may include generating training datasets by combining the simulation model with a mass and energy balance of the at least one food product processing device. Defining the machine learning model may include training the machine learning model based on training datasets. The machine learning model may be a reinforcement model achieving reward reinforcement based on the simulation model. In some embodiments, reward reinforcement may be determined based on at least one of size, surface attrition, texture, bulk density, and curvature of the food product.

According to another aspect of the present disclosure, a method of operating a system for producing food product including one or more food product processing devices for processing food material as food products may include evaluating image information of at least one of food material and food product to determine a bulk density value; operating a machine learning model to determine, in real-time, desired setting of at least one control parameter for the at least one food product processing device based on the determined bulk density value; and controlling the at least one food product processing device to have the at least one desired control parameter.

In some embodiments, the method may further include defining the machine learning model based on a simulation model for governing control of the at least one food product processing device. The method may further include generating the simulation model based on a physical simulation of food material within the at least one food product processing device. Generating the simulation model based on a physical simulation of food material may include defining the simulation model from a reduced order model based on the physical simulation of the at least one food product processing device. In some embodiments, generating the simulation model may include generating training datasets by combining the simulation model with a mass and energy balance of the at least one food product processing device.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

Figure 1:
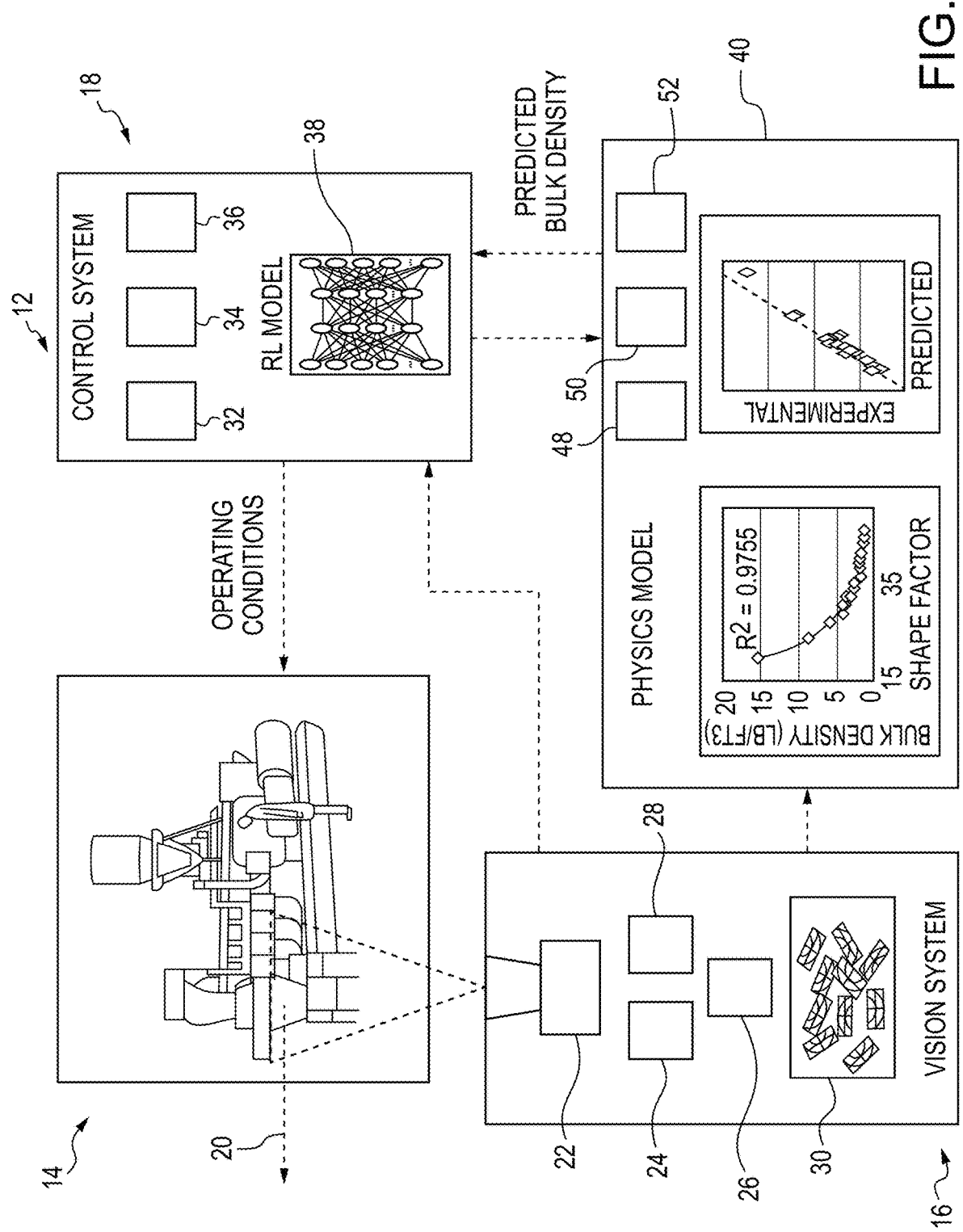
Figure 2B:
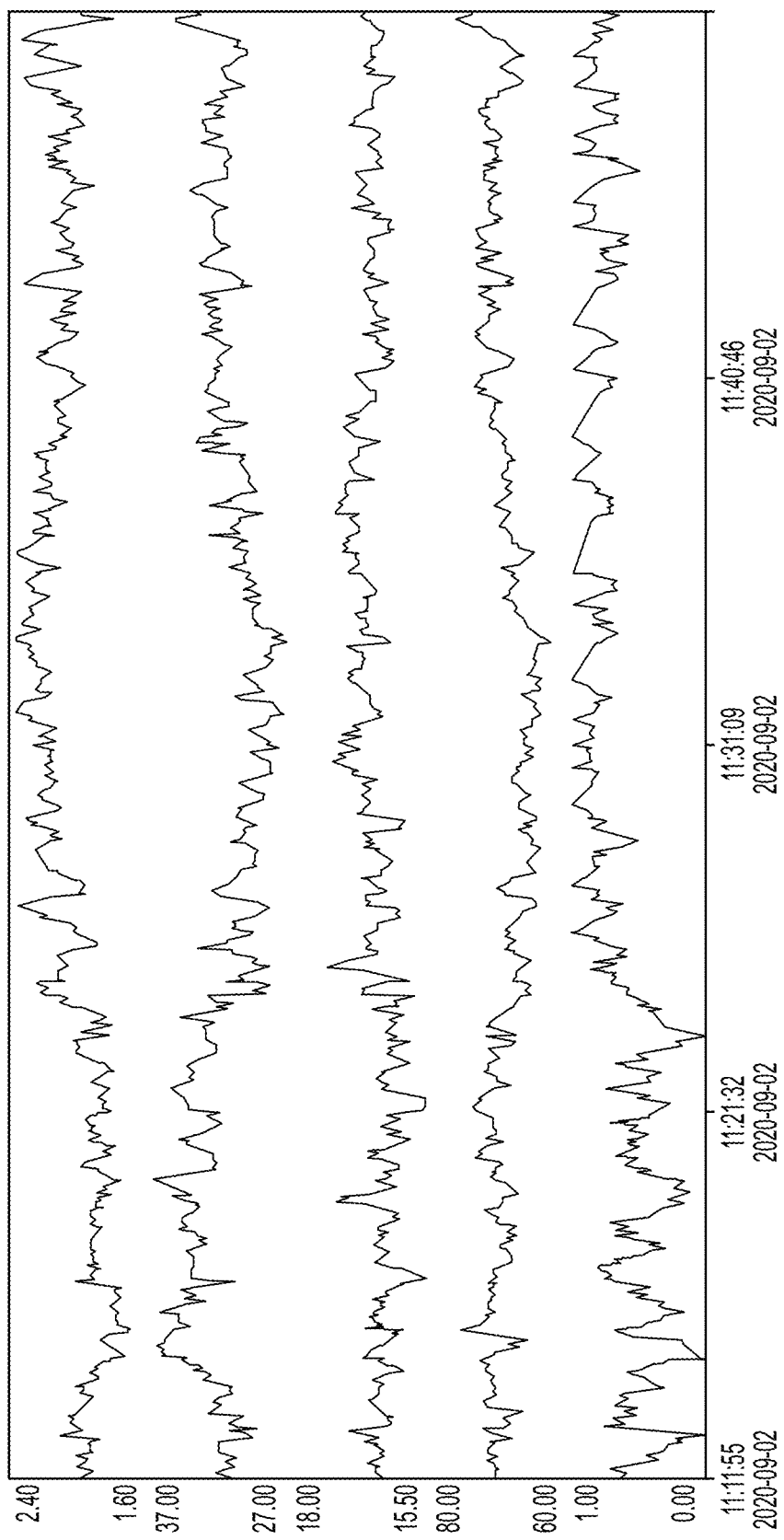
Figure 2D:
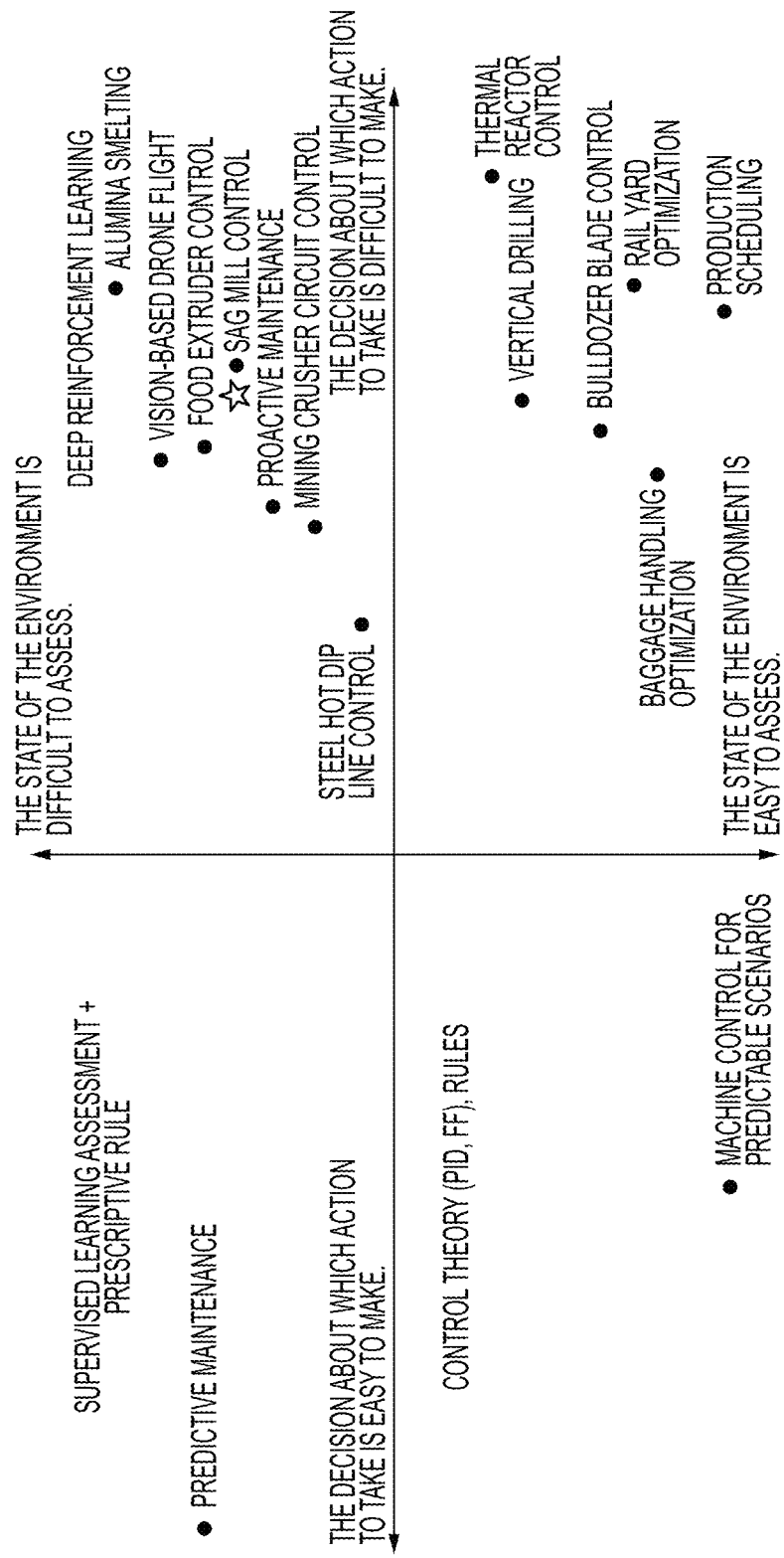
Figure 4:
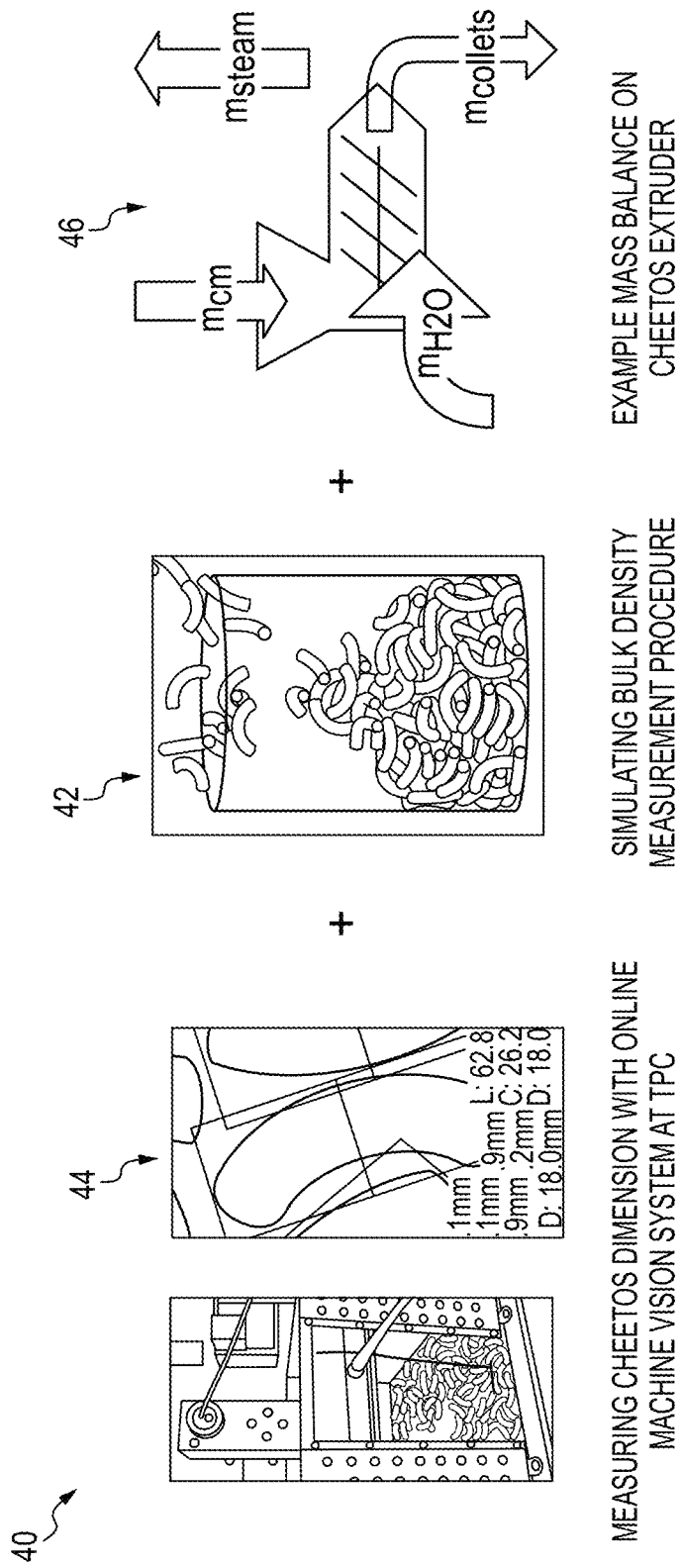
Figure 5:
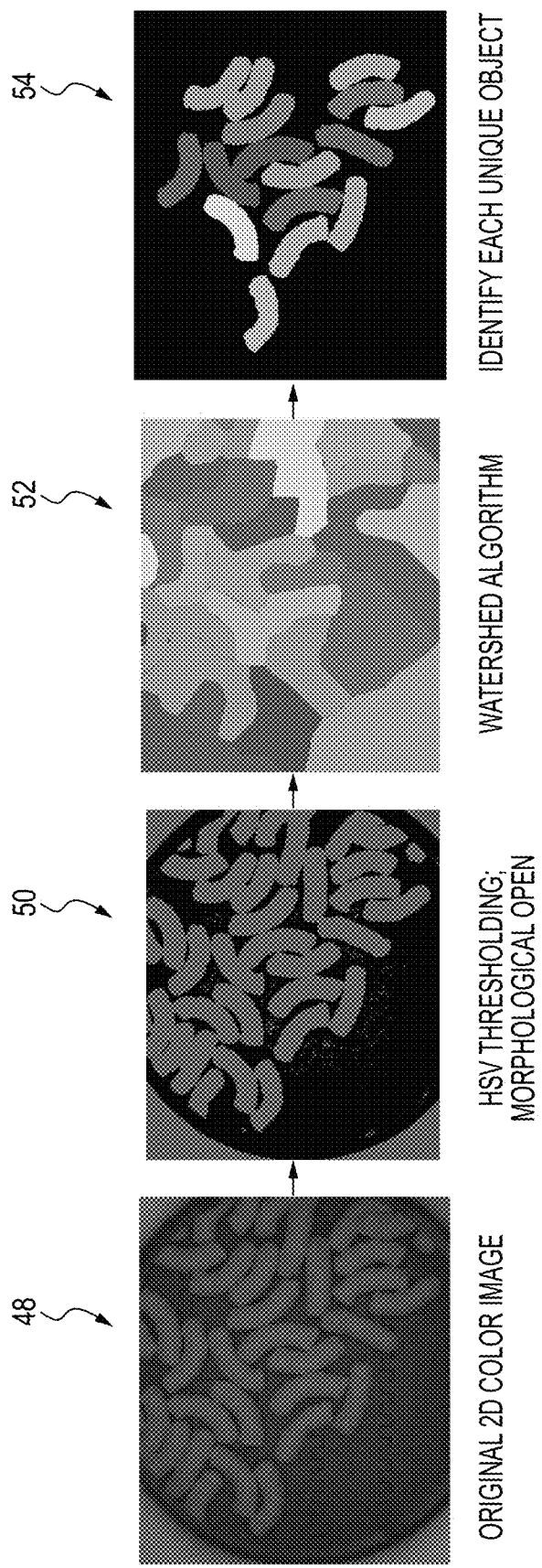
Figure 7:
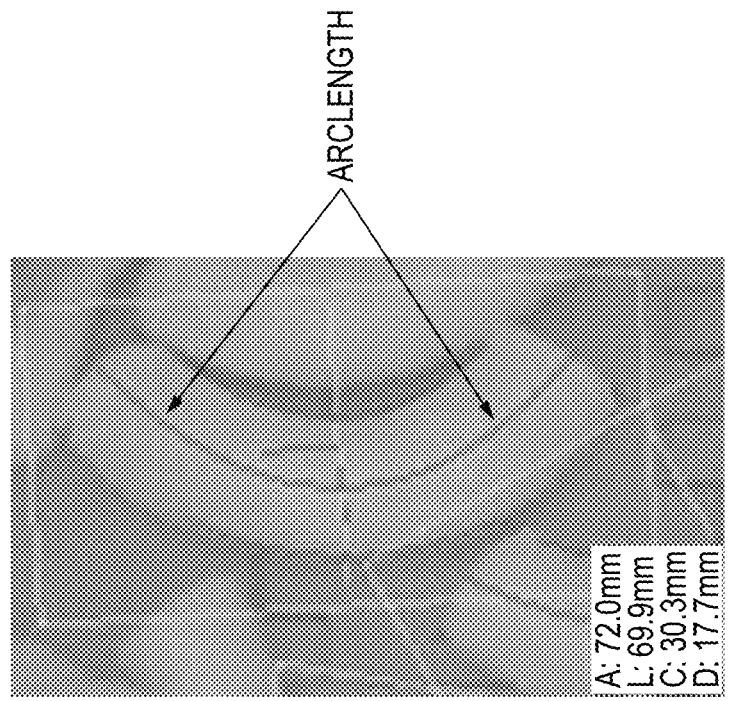
Figure 6:
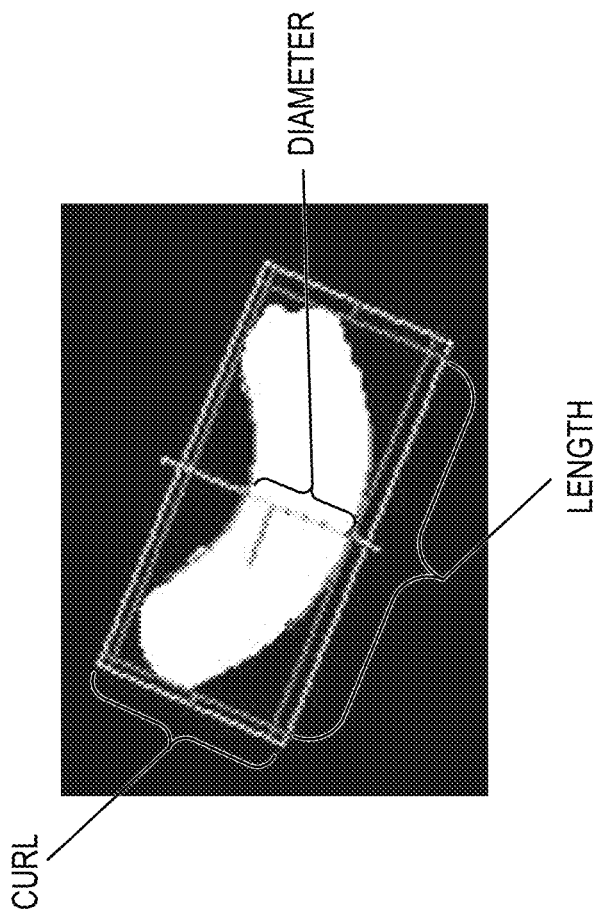

The detailed description particularly refers to the accompanying figures in which:

FIG. 1 is a diagrammatic schematic view of a food product processing system including a food product processing device, embodied as an extruder for extruding food product, a bulk density evaluation system, and a control system for governing operation of the food product extruder, and showing that the control system includes a machine learning model;

FIG. 2A is pictorial view of a manual datasheet for manual bulk density measurements;

FIG. 2B is a graph indicating an example of frequency of adjustment to a number of control variables of the food product processing system of FIG. 1;

FIG. 2C is a screen shot of a user interface indicating an instantaneous control operation for adjustment of parameters for the food product extruder of the food product processing system of FIG. 1;

FIG. 2D is plot of various machine learning scenarios indicating a coordinated level of difficulty of various factors related to machine learning concerning control of the food product processing system of FIG. 1;

FIG. 3 is a pictorial view of a manual operation for bulk density evaluation for the food product extruder of the food product processing system of FIG. 1;

FIG. 4 is a diagrammatic view of a process of bulk density evaluation of the food product processing system of FIG. 1;

FIG. 5 is a diagrammatic view of image evaluation in consideration of food item within a batch, applied in bulk density evaluation;

FIG. 6 is a pictorial view of a food item indicating dimensions which can be considered for bulk density evaluation;

FIG. 7 is another pictorial view of a food item indicating dimensions which can be considered for bulk density evaluation; and FIG. 8 is a flow diagram indicating a process of operation for the food processing system of FIG. 1.

DETAILED DESCRIPTION

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

In high volume food manufacturing, certain product attributes can be important to defining product quality. However, measuring underlying attributes by traditional methods, such as by offline, manual, and/or infrequent techniques can lead to efficiency challenges in process control. For example, in high volume food production, the bulk density of food products can be an important attribute which indicates the product's texture and/or bag fill.

Traditionally, bulk density is measured manually, for example, using a specific volume container which can be filled with sample product and weighed. In traditional production, such manual measurement may be performed once per hour of production, for example. Yet, the product quality can drift outside of specification rapidly under common disturbances. Increasing the frequency of measurement can mitigate such risks, but can fail to foreclose the issue. Persistent drifting of quality, such as out of specification bulk density, can lead to poor product quality and/or sub-optimal bag fill. As an example, overfilling bags can lead to packaging and/or product waste, while under-filling can lead to poor product impression by the consumer.

Real-time, or near real-time bulk density evaluation and control can be implemented to overcome the challenges of food production, and particularly, high volume food production. Referring to FIG. 1, a food processing system 12 is shown for operation to process food material into food product. The food processing system 12 includes a food product processing device 14, illustratively embodied as an extruder. The system 12 includes a bulk density evaluation system 16 that may incorporate image analysis of food materials and/or product to determine a bulk density value, and a control system 18 for governing operations of the food product processing device 14 based on the determined bulk density value. As discussed in additional detail, the control system 18 comprises a machine learning model configured to determine, in real-time, at least one control parameter for the food product processing device 14, based on the determined bulk density value.

Process control of the food product processing device 14 can be a rapidly changing, multi-variable problem. For food processing, bulk density can provide an indicator for various desirable food product outcomes. However, determining bulk density can be challenging, particularly in real-time operations. Traditionally, bulk density determinations have been performed manually, by discrete sampling and analysis. For example, as shown in FIGS. 2A & 3, a manual process and scorecard can be used to record analytical measurements for bulk density determination. Such manual operations are not conducive to the rapid changes in food processing and are limited by their own time requirements. By comparison, with real-time (or near real-time) control of the extruder 14, continuous process control can be achieved as suggested in FIG. 2B.

Turning back to FIG. 1, food material is provided into the extruder 14 for extrusion into food product. For example, corn meal as food material is provided to the extruder 14 for extrusion to form cheese curls as the food product, such as Cheetos® Puffs, as marketed by Frito-Lay North America, of Plano, Texas. The food product generated by the extruder 14 is shown in FIG. 1 indicated by stream 20, which may represent continuous or batch processing. The evaluation system 16 can capture visual information of the food material and/or product from the extruder 14 for consideration to determine the bulk density. The evaluation system 16 illustratively includes a camera 22 arranged to capture visual images of the food product from the extruder 14. In some embodiments, bulk density may be determined based on visual information regarding food material still within the extruder 14, with or without visual information regarding the food product output from the extruder 14.

The evaluation system 16 illustratively includes a vision system for analyzing visual information. The vision system includes a processor 24 for executing instructions stored on memory 26, and communications circuitry 28 for communicating with other systems as directed by the processor 24. The vision system conducts analysis of the visual images captured by the camera 22 for determining bulk density.

The evaluation system 16 includes a neural network 30 for analysis of visual information. The neural network 30 illustratively resides on the vision system for analysis of image information from the camera 22 for determining bulk density. The neural network 30 is illustratively embodied as a convolutional neural network (CNN), although in some embodiments, any suitable manner of artificial intelligence may be applied.

The CNN is illustratively stored on memory 26 for execution by the processor 24. The CNN illustratively comprises a number of layers, including at least one convolutional layer, for analyzing image data passed through each layer successively to generate an output. The CNN is illustratively trained by analysis of baseline images of food product from the extruder 14 to develop a ground truth (system of layers) for evaluation of bulk density as a numerical output.

In the illustrative embodiment, the CNN is formed as a regression model suitable for continuous analysis of food (food material and/or product) from the extruder 14. Configuration of the CNN to provide numerical output in lieu of traditional CNN classification of image data can assist in enabling continuous analysis. Continuous analysis by the CNN can reduce and/or avoid the need for massive amounts of training data to be analyzed in order to capture the extent of variations of food which can be experienced. The bulk density output from the evaluation system 16 can be communicated to the control system 18 for use in control system operations.

The control system 18 provides governing control of the operations for the food product processing device (e.g., extruder) 14. In the illustrative embodiment, the control system 18 determines the desired operational parameters of the food product processing device 14, in real-time, based on the bulk density determination communicated from the evaluation system 16. For example, the operational parameters for control of the exemplary extruder 14 by the control system 18 can include one or more of meal feed rate, water feed rate, screw rotation speed, barrel temperatures and pressures, and/or cutter speed as suggested in FIG. 2C.

As suggested in FIG. 2D, devices, systems, and methods within the present disclosure for managing the nature and/or complexities of real-time process control for the extruder 14 can be characterized as deep reinforcement learning as indicated by the star icon. Such problems can have elevated difficulties in assessing the state of the measurement to be considered and/or elevated difficulties in the decision about which control response action should be made.

Returning to FIG. 1, the control system 18 includes a processor 32, memory 34, and communication circuitry 36 for conducting control system operations. The processor 32 executes instructions stored on memory 34, and can communicate signals with other devices and/or systems, such as the food product processing device 14 and/or evaluation system 16, via the communication circuitry 36. The control system 18 includes a machine learning model 38 for determining real-time settings for the food product processing device 14.

The machine learning model 38 of the control system 30 is illustratively embodied as a reinforcement learning model for determining real-time settings. The reinforcement learning model is illustratively stored on memory 34 for execution by processor 32 to conduct operations of the control system 18. The reinforcement learning model is illustratively defined according to training with a simulation model 40 of the control system 18.

The simulation model 40 illustratively comprises a physical simulation of food (material and/or product) through and/or from the food product processing device 14. Referring to FIG. 4, the physical simulation 42 is illustratively applied in the simulation model 40 together with line data (image data) 44 from food (material and/or product) from the extruder 14, and a mass & energy balance 46, as a reduced order model (ROM) for defining the reinforcement learning model of the control system 18. In the example of extrusion, the physical model is illustratively embodied as a discrete element model (DEM) of physical movement of the food through and/or from the extruder 14. For example, the DEM model may simulate the physical operation of the food material through a particular one or more points within the extruder 14.

The DEM is illustratively combined or supplemented with line data 44 and the mass and energy balance 46 to produce the reduced order model. For example, the line data 44 may include one or more of size, surface attrition, texture, bulk density, and/or curvature, which may be indicated by the image information as discussed above by the evaluation system. The line data may be selected in advance to correspond with a predetermined variability of bulk density, for example, within 3% of design bulk density (or any other suitable pre-selected amount), and may be provided from the memory 44. The reduced order model of the simulation model 40 provides a physical simulation combining physical modelling 42 with real world line data 44 and energy & mass balance 46 to assemble realistic datasets for training the machine learning model 38 of the control system 18.

The training datasets can be applied to define the machine learning model 38 according to numerical coefficients for operation, so that the machine learning model 38 can govern operation of the extruder 14 based on the bulk density provided by the evaluation system 16. For example, the machine learning model may be defined based on sphericity and/or excluded volume, wherein $$\text{sphericity} = \frac{\text{surface area based on } SEVD}{\text{actual surface area}} \text{ and excluded volume} = \frac{\text{particle volume}}{\text{bounding box volume}} * \text{curl},$$

where SEVD indicates Sphere Equivalent Volume Diameter, and bounding box volume indicates the minimum closed box volume that completely contains the shape. In the illustrative embodiment, the machine learning model 38 is formed as a reinforcement model, for example, but without limitation, a Q-learning or deep reinforcement model, achieving reward reinforcement based on determination of at least one of sphericity and excluded volume. The factors for determining sphericity and/or excluded volume as defined above may include at least one of size surface attrition, texture, bulk density (if known), and/or curvature of the food. In some embodiments, the machine learning model 38 may be formed to include any suitable manner of model, for example but without limitation, supervised, quasi-supervised, and/or unsupervised learning models, such as linear regression, logistic regression, decision tree, SVM, Naive Bayes, kNN, k-means, random forest, dimensionality reduction algorithms, gradient boosting algorithms (e.g., GBM, XGBoost, LightGBM, CatBoost) style models. Accordingly, the machine learning model 38 can be developed based on the training datasets.

Returning to FIG. 1, the simulation model 40 is illustratively embodied as a system including a processor 48, memory 50, and communication circuitry 52 for conducting simulation system operations. The processor 48 executes instructions stored on memory 50, and can communicate signals via other devices, such as the processor 32, via the communication circuitry 52. In some embodiments, the processors, memory, and/or communications circuitry of the simulation model 40 may be partly or wholly shared with the processor 32, memory 34, and/or communication circuitry 36 and/or processor 24, memory 26, and/or communication circuitry 28.

In the illustrative embodiment, the simulation model 40 can undertake validation of its training datasets in comparison to baseline measurements for bulk density. The validation can include comparison of predictions by the reduced order model for bulk density with ground truth validation values. For example, one or more extruders can be operated at various operating conditions to change the actual bulk density of the food, and the actual bulk density can be measured as ground truth validation values. The operating conditions can be input to the reduced order model, and the reduced order model can predict the bulk densityvalue for those operating conditions. Close correlation of the reduced order model predictions with the measured ground truth validation values can be used to validate the accuracy and/or precision for prediction by the reduced order model.

The machine leaning model of the control system 18 is illustratively embodied as a reinforcement learning (RL) model. The RL model can act as the agent providing action outputs to the extruder 14, for example, real-time adjustment of extruder operational parameters such as meal feed rate, water feed rate, screw rotation speed, barrel temperatures and pressures, and/or cutter speed. The extruder 14, and more precisely the food (food material and/or food product) of the extruder 14, can provide the environment for evaluation by the evaluation system 16. The RL model receives the state of the environment as the bulk density value from the evaluation system 16 and generates the appropriate reward reinforcement based on the bulk density value.

In the illustrative embodiment, the RL model of the control system 18 is defined by learning based on the training data sets from the simulation model 40. The definition of the RL model may be updated based on either or both of the bulk density values provided by the evaluation system 16 and the simulation model 40. In some embodiments, definition of the RL model may be performed by combined application of the evaluation system 16 and the simulation model 40.

Referring now to FIG. 5, the evaluation system 16 can conduct image evaluation to determine the bulk density, in real-time. An exemplary 2D color image 48 of food product is captured by the evaluation system 16. The evaluation system 16 can analyze the image 48 to target the subject food items. For example, at block 50, the evaluation system 16 illustratively conducts hue, saturation, value (HSV) thresholding to target the subject food against background. The evaluation system 16 can analyze the image 48 to separate object items. For example, at block 52, the evaluation system 16 illustratively conducts watershed analysis applying a watershed algorithm for segmentation to distinguish different food items from each other. In some embodiments, watershed analysis may be performed on the HSV threshold evaluated image of block 50. The evaluation system 16 may identify unique objects. For example, at block 54, the evaluation system 16 can identify each unique food item based on the HSV thresholding and/or watershed analysis.

Referring now to FIGS. 6 & 7, the evaluation system 16 can determine characteristic features of the food (product or material). For example, in the exemplary case of the cheese curls as suggested in FIG. 6, the evaluation system 16 illustratively determines one or more of the curl, diameter, and/or length of a cheese curl. As shown in FIG. 7, the characteristic features for the exemplary cheese curl illustratively includes arc length, defined as the length of the cheese curl along its curvature. The curl of the cheese curl includes the depth of curvature, the diameter includes the measure of curvature, and the length includes the linear extent of the cheese curl. Other food items may have one or more other characteristic features, such as extent of twist, thickness, symmetry, and/or texture.

Referring now to FIG. 8, an operation of the food processing system 12 is shown as flow diagram 60. As discussed, the simulation model can be generated and a machine learning module defined. Image evaluation and bulk density determination can be conducted, and control commands can be generated.

In box 62, a simulation model may be generated. As mentioned, the simulation model may comprise a physical simulation of food (material and/or product) through and/or from the food product processing device 14. The simulation model may include a reduced order model providing physical simulation combining physical modelling with data, such as real world line data 44 and energy & mass balance 46, to assemble training datasets.

In box 64, a machine learning model may be defined. As discussed, the machine learning model may be defined based on the training datasets from the simulation model generated in box 62. The training datasets can be applied to define the machine learning model according to numerical coefficients for operation, so that the machine learning model can govern operation of the extruder 14, based on one or more of the features, such as size, surface attrition, texture, bulk density, and/or curvature of the food (food material and/or food product) determined by the evaluation system 16. Such features may be applied in terms of their contribution to, for example as predicted by, sphericity and/or excluded volume.

In box 66, image evaluation can be conducted. The evaluation system 16 can conduct image evaluation. In the illustrative embodiment, the evaluation system 16 can capture and analyze image information of food (food material and/or food product) to determine characteristic features of the food.

In box 68, the a bulk density determination can be conducted. In the illustrative embodiment, the evaluation system 16 can determine a bulk density value of the food based on the characteristic features determined from the operations in box 66. In some embodiments, the operations of boxes 66 and 68 can be conducted simultaneously and/or by comingled process. In some embodiments, determination of bulk density may be performed by the control system 18.

In box 70, control commands can be determined. The control system 18 can determine control commands for the extruder 14 based on the bulk density determined by operations in box 68. As discussed, the control system 18 may determine to adjust (or not to adjust) meal feed rate, water feed rate, extruder speed, barrel temperature, and/or cutter speed.

In some embodiments, the operations of boxes 62 and/or 64 may be omitted and/or conducted only occasionally based on need and/or performance to update the models. The operations of boxes 66, 68, and/or 70 may be conducted repeatedly and/or cyclically, to provide real-time process control of the extruder operations based on the bulk density value.

Accordingly, bulk density food processing control can be implemented, reducing the risk of poor quality products and/or improper bagging. Implementation of disclosed aspects can provide real-time bulk density as a virtual bulk density sensor and/or response, to efficiently and/or effectively control high volume food processing equipment.

Within the present disclosure, the camera of the evaluation system 16 is shown as a single camera adapted to capture images within the visual spectrum and additionally adapted to capture images in the near infrared (NIR) spectrum, but may include any suitable number and/or manner of image capture devices within a camera system for capturing image information of food, for example, multiple cameras for capturing images of food from one or more extruders.

Within the present disclosure various hardware indicated may take various forms. Examples of suitable processors may include one or more microprocessors, integrated circuits, system-on-a-chips (SoC), among others. Examples of suitable memory, may include one or more primary storage and/or non-primary storage (e.g., secondary, tertiary, etc. storage); permanent, semi-permanent, and/or temporary storage; and/or memory storage devices including but not limited to hard drives (e.g., magnetic, solid state), optical discs (e.g., CD-ROM, DVD-ROM), RAM (e.g., DRAM, SRAM, DRDRAM), ROM (e.g., PROM, EPROM, EEPROM, Flash EEPROM), volatile, and/or non-volatile memory; among others. Communication circuitry includes components for facilitating processor operations, for example, suitable components may include transmitters, receivers, modulators, demodulators, filters, modems, analog to digital converters, operational amplifiers, and/or integrated circuits.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A system for producing food product, the system comprising:
   at least one food product processing device for extruding food material into food products;
   a bulk density evaluation system for analyzing image information of at least one of food material and food product to determine a bulk density value; and
   a control system configured to govern operation of the at least one food product processing device based on the determined bulk density value, wherein the control system comprises a machine learning model configured to determine, in real-time, at least one control parameter for the at least one food product processing device, based on the determined bulk density value, wherein the machine learning model is defined based on a simulation model comprising a physical simulation of food material within the at least one food product processing device and real world line data of the food product processing device.

2. The system of claim 1, wherein the at least one control parameter is selected from the group comprising meal feed rate, water feed rate, screw speed, barrel temperature, barrel pressure, and cutter speed.

3. The system of claim 1, wherein the physical simulation of food material is applied as a reduced order model and the simulation model comprises the physical simulation defined by the reduced order model.

4. The system of claim 1, wherein the machine learning model comprises a reinforcement learning model.

5. The system of claim 4, wherein the simulation model is configured to provide training datasets applied by the machine learning model to generate numerical coefficients for operation of the machine learning model to govern operation of the at least one food product processing device based on the determined bulk density value.

6. The system of claim 5, wherein the training datasets applied by the machine learning model are generated in the simulation model.

7. The system of claim 6, wherein the machine learning model is formed as a reinforcement model achieving reward reinforcement based on the simulation model to define the reinforcement model.

8. The system of claim 7, wherein reward reinforcement is determined based on at least one of size, surface attrition, texture, bulk density, and curvature of the food product.

9. The system of claim 5, wherein the simulation model is combined with a mass and energy balance of the at least one food product processing device to provide the training datasets.

10. The system of claim 1, wherein the bulk density evaluation system comprises at least one camera for capturing visual images of the food product for analysis.

11. The system of claim 10, wherein the at least one camera is arranged to capture visual images of food material within the at least one food product processing device.

12. The system of claim 10, wherein the at least one camera is arranged to capture visual images of food product produced from the at least one food product processing device.

13. The system of claim 10, wherein the bulk density evaluation system comprises a convolution neural network for analysis of image information, and the output of the convolutional neural network yields determination of at least one of size, surface attrition, texture, bulk density, and curvature of the food product as a numerical output value.

14. The system of any claim 10, wherein the food product produced by the at least one food product processing device is produced in a prepared form, safe for consumption.

15. A method of operating a system for producing food product including one or more food product processing devices for producing food material as food products, the method comprising:
  generating a simulation model based on a physical simulation of food material within the at least one food product extrusion device;
  defining a machine learning model based on the simulation model for governing control of the at least one food product processing device;
  evaluating image information of at least one of food material and food product to determine a bulk density value;
  operating the defined machine learning model to determine, in real-time, desired setting of at least one control parameter for the at least one food product processing device based on the determined bulk density value, wherein the machine learning model is defined based on the simulation model comprising the physical simulation of food material within the at least one food product processing device and real world line data of the food product processing device; and
  controlling the at least one food product processing device to have the at least one desired control parameter.

16. The method of claim 15, wherein each of evaluating image information of at least one of food material and food product, operating the defined machine learning model to determine at least one control parameter in real-time, and controlling the at least one food product processing device to have the at least one desired control parameter occurs recurrently.

17. The method of claim 15, wherein generating the simulation model based on a physical simulation of food material includes defining the simulation model from a reduced order model based on the physical simulation of the at least one food product processing device.

18. The method of claim 15, wherein generating the simulation model includes generating training datasets by combining the simulation model with a mass and energy balance of the at least one food product processing device.

19. The method of claim 15, wherein defining the machine learning model includes training the machine learning model based on training datasets.

20. The method of claim 15, wherein the machine learning model is a reinforcement model achieving reward reinforcement based on the simulation model.

21. The method of claim 20, wherein reward reinforcement is determined based on at least one of size, surface attrition, texture, bulk density, and curvature of the food product.

22. A method of operating a system for producing food product including one or more food product processing devices for processing food material as food products, the method comprising:
  evaluating image information of at least one of food material and food product to determine a bulk density value;
  defining the machine learning model based on a simulation model for governing control of the at least one food product processing device, and operating the machine learning model to determine, in real-time, desired setting of at least one control parameter for the at least one food product processing device based on the determined bulk density value, wherein the machine learning model is defined based on the simulation model comprising the physical simulation of food material within the at least one food product processing device and real world line data of the food product processing device; and
  controlling the at least one food product processing device to have the at least one desired control parameter.

23. The method of claim 22, wherein generating the simulation model based on a physical simulation of food material includes defining the simulation model from a reduced order model based on the physical simulation of the at least one food product processing device.

24. The method of claim 22, wherein generating the simulation model includes generating training datasets by combining the simulation model with a mass and energy balance of the at least one food product processing device.

* * * * *